United States Patent [19]
Weiss

[11] Patent Number: 5,873,813
[45] Date of Patent: Feb. 23, 1999

[54] METHOD AND APPARATUS FOR PRODUCING AND MAINTAINING A PENILE ERECTION

[75] Inventor: Robert R. Weiss, Chicago, Ill.

[73] Assignee: B.S.W. Partnership, Skokie, Ill.

[21] Appl. No.: 19,058

[22] Filed: Feb. 5, 1998

[51] Int. Cl.[6] .................................................. A61F 5/00
[52] U.S. Cl. ............................ 600/38; 600/40; 600/39; 24/271; 24/20 R; 24/20 S; 24/274 P
[58] Field of Search .................... 600/38–40; 24/271, 24/20 R, 20 S, 274 P

[56] References Cited

U.S. PATENT DOCUMENTS

| | | | |
|---|---|---|---|
| 4,203,432 | 5/1980 | Koch | 600/38 |
| 4,305,179 | 12/1981 | Sakurada | 24/20 R |
| 4,425,682 | 1/1984 | Hashimoto et al. | 24/20 S |
| 4,723,538 | 2/1988 | Stewart et al. . | |
| 4,969,240 | 11/1990 | Sauer | 24/20 R |
| 4,995,381 | 2/1991 | Marmar et al. | 600/39 |
| 5,327,910 | 7/1994 | Fiynn | 600/38 |
| 5,336,157 | 8/1994 | Hale . | |
| 5,344,389 | 9/1994 | Walsdorf et al. . | |
| 5,628,329 | 5/1997 | Bennett et al. | 600/39 |

*Primary Examiner*—Robert L. Nasser
*Assistant Examiner*—Michael Astorino
*Attorney, Agent, or Firm*—Andrus, Sceales, Starke & Sawall

[57] ABSTRACT

An apparatus for producing and maintaining a penile erection in a male suffering from erectile dysfunction includes a resilient ring member defining an inner opening through which the penis is inserted. The inside circumferential surface adjacent the inner opening is supple and adapted to contact the shaft of the penis. The cross-sectional area of the inner opening is adjustable between a minimum cross-sectional area which is sized sufficiently small to restrict the return venous blood flow from the penis to the torso (i.e. restrict excessive venous leakage) and larger cross-sectional areas. The apparatus includes a pair of spaced apart handles extending outwardly from the resilient ring member which allow the user of the apparatus to quickly adjust the cross-sectional area of the inner opening. In use, a flaccid penis is inserted through the inner opening of the resilient ring member and the resilient ring member is placed in the closed position at the base of the penis adjacent the torso. With the resilient ring member in the closed position, the apparatus is moved along the penis shaft away from the torso thereby increasing the amount of engorgement of the portion of the penis on the side of the apparatus opposite the torso. The apparatus is opened and quickly moved again to the base of the penis adjacent the torso. Again, the apparatus is moved along the penis in the closed position away from the torso to incrementally capture more blood within the penis and increase engorgement, thus producing a firm erection suitable for sexual penetration and enjoyment. After a sufficient amount of blood has been captured within the penis to produce a suitable erection, the resilient ring is placed at the base of the penis in the closed position adjacent the torso to maintain the erection.

3 Claims, 2 Drawing Sheets ern is in the fully closed position and larger cross-sectional areas when the resilient ring member is in a partially or fully open position. The minimum cross-sectional area of the inner opening of the resilient ring member is sized sufficiently small to restrict return venous blood flow from the penis to the torso. Thus, the resilient ring member can be used to restrict venous leakage when the resilient ring member is in the closed position. The inside circumferential surface of the resilient ring member is preferably supple and adapted to contact the skin on the shaft of the penis. The apparatus also preferably includes a pair of spaced apart handles extending outwardly from the resilient ring member which are used to adjust the cross-sectional area of the inner opening. In the preferred embodiment, the resilient ring member is biased to remain in the closed position such that the cross-sectional area of the inner opening through the resilient ring member is at the minimum cross-sectional area and the handles remain spaced apart. The ring member is opened to increase the cross-sectional area of the inner opening through the ring member by squeezing the handles towards each other.

METHOD AND APPARATUS FOR PRODUCING AND MAINTAINING A PENILE ERECTION

FIELD OF THE INVENTION

The invention relates to a method and apparatus of producing and maintaining a penile erection in males suffering from erectile dysfunction, otherwise known as impotence.

BACKGROUND OF THE INVENTION

Erectile dysfunction is a condition in which a male is not capable of attaining an erect penis that is sufficiently rigid for sexual penetration or sexual satisfaction. It is a common problem, especially in older males. Normally, when a man becomes sexually aroused his penis becomes engorged with blood thereby not only increasing the size of the penis, but also making the penis rigid and erect to enable sexual penetration. An average flaccid penis is, for example, between 3 to 4 inches long, and it increases in length to about 5 to 7 inches when erect. An erect penis contains 6 to 7 times the blood volume of a flaccid penis. During erection, the arterial rate of blood flowing into the penis is greater than the returning venous rate of blood flowing from the penis to the torso, and this leads to accumulation of blood within the corpus cavernosum and the resulting engorgement of the penis.

There are potentially many physical and psychophysical reasons for erectile dysfunction, but most cases involve excessive venous leak from the penis in one form or another. The amount of venous leak varies among men having erectile dysfunction, and thus the extent of the dysfunction varies. For example, some men are able to achieve erection, however, are likely to loose the erection before ejaculation. Surgical techniques for reducing or eliminating venous leak have proven to be largely unreliable.

It is well known that the penile arteries are located deep within the penis, and the veins which return blood to the torso are located principally adjacent the skin. Therefore, it has long been known to use constrictor rings or the like to constrict the base of the penis in order to reduce venous leak and enhance the maintenance of erection.

Besides constrictor rings, there are several types of physical treatment for impotence. The various treatments include drugs and pharmaceuticals, prostheses that may be inserted into the penis (for example inflatable rods), and vacuum devices which draw blood into the corpus cavernosum causing the penis to become engorged and erect coupled with an elastic constrictor ring placed around the base of the penis in order to maintain the erection. Obviously, some of these treatments have side effects, whereas others are cumbersome and/or somewhat expensive.

BRIEF SUMMARY OF THE INVENTION

The invention is a method of producing and maintaining a penile erection in a male suffering from erectile dysfunction which involves the use of a simple, inexpensive mechanical apparatus. If the apparatus is sized appropriately and the method implemented properly, a male suffering from erectile dysfunction is able to obtain a firm erection within 1 to 10 minutes depending on the extent of sexual arousal.

The apparatus is a resilient ring member having an inner opening through which the penis is inserted. The cross-sectional area of the inner opening is adjustable between a minimum cross-sectional area when the resilient ring mem- The apparatus is especially designed to produce and maintain a penile erection in a male suffering from erectile dysfunction in the following manner. The resilient ring member is opened to increase the cross-sectional area of the inner opening through the ring member. The flaccid penis is then inserted through the inner opening of the resilient ring member, and the ring member is placed at the base of the penis adjacent the torso. The resilient ring member is closed so that the ring member restricts the return venous blood flow away from the penis into the torso (i.e. restricts excessive venous leakage). In the closed position, the ring member is moved along the penis shaft away from the torso preferably 1 to 2 inches, thereby increasing the amount of engorgement of the portion of the penis on the side of the resilient ring member opposite the torso. The resilient ring member is then opened and quickly moved again to the base of the penis adjacent to the torso. Again, the resilient ring member is closed and moved along the shaft of the penis away from the torso to incrementally capture blood within the penis to facilitate engorgement. These steps are repeated as necessary to capture enough blood within the penis on the side of the resilient ring member opposite the torso to produce a firm erection suitable for sexual intercourse and enjoyment. When moving the ring member, it is preferred that the ring member not slide with respect to the skin on the penis. Rather, it is preferred that the skin move along with the ring member. After enough blood has been captured within the penis to produce a firm erection, the resilient ring member is placed at the base of the penis adjacent the torso in a closed position to maintain the erection. It is important that doctors be involved in sizing the apparatus for the particular patient so that erection can be obtained efficiently and maintained adequately without pain.

In its preferred construction, the apparatus comprises a substantially circular spring made of resilient wire which is covered by a supporting cloth mesh substrate that is wrapped at least partially around the circular spring. The circular spring and the cloth mesh are encapsulated by an elastomer such as medical grade silicone. The silicone forms a supple, non-slippery inside circumferential surface for the resilient ring member which facilitates engagement with the penis. The substantially circular spring and the handles of the apparatus are preferably made from a single piece of continuous resilient wire. When the apparatus is closed, the handles are aligned through a center of the inner opening of the resilient ring member, and the angle between the handles is preferably approximately 90°. With this configuration, the handles can be used to open and close the resilient ring member quickly and repeatably. It is intended that the apparatus be reusable, and therefore the wire for the substantially circular spring should be sufficiently strong and have sufficient resilience.

It should be apparent to those skilled in the art that an apparatus in accordance with the invention is small, and this allows the apparatus to be conveniently carried by a person in their pocket or the like if they so desire. The apparatus and its method of use also provides a relatively inexpensive solution for erectile dysfunction, at least for some males. This solution is available without having to endure the side effects or inconvenience of other treatments or devices.

It should also be pointed out that the embodiment of the invention shown in the drawings also restricts the passage of semen from the penis when climax occurs, unless the resilient ring member is open for manual release. Note that a user of the apparatus need not terminate sexual relations upon the occurrence of a climax.

Other features and advantages of the invention may be apparent to those skilled in the art upon inspecting the following drawings and description thereof.

DETAILED DESCRIPTION OF THE DRAWINGS

FIGS. 1 through 5 illustrate an apparatus 10 for producing and maintaining a penile erection in a male suffering from erectile dysfunction in accordance with the preferred embodiment of the invention. The apparatus 10 includes a resilient ring member 12 which defines a generally circular inner opening 14 through which the penis is inserted. The apparatus 10 also includes handles 16A and 16B which extend outwardly from the resilient ring member 12.

Figure 1:
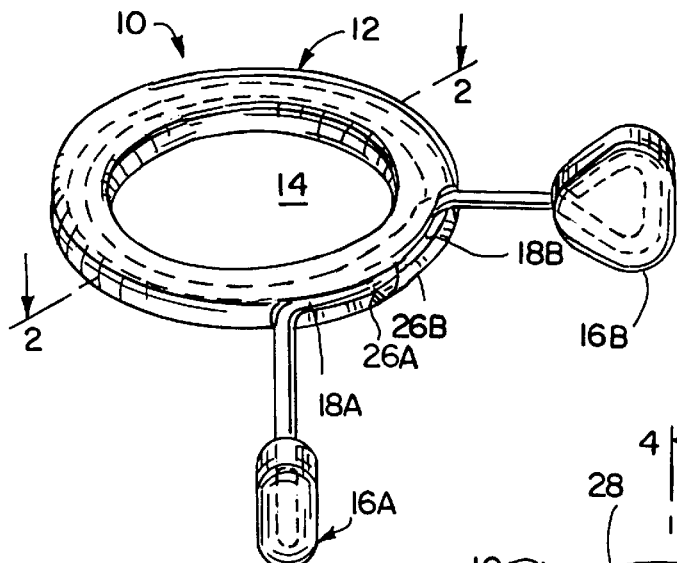
FIG. 1 is a perspective view of an apparatus for producing and maintaining a penile erection in accordance with the invention.
Figure 2:
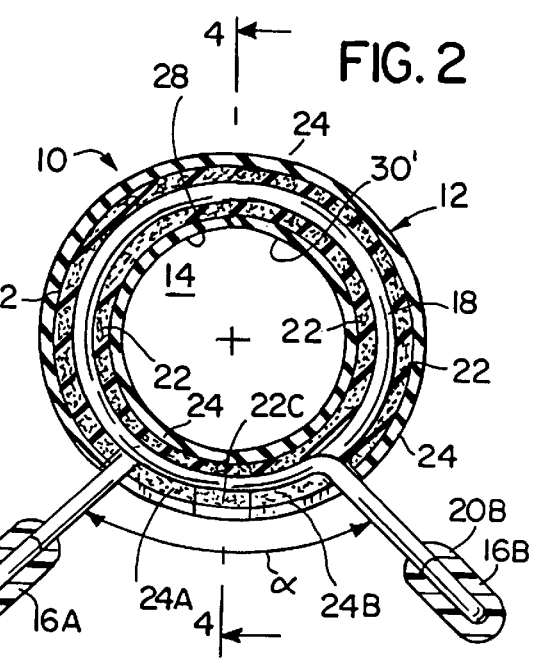
FIG. 2 is a planar sectional view of an apparatus in accordance with the invention taken from the point of view of arrows 2—2 in FIG. 1.
Figure 4:
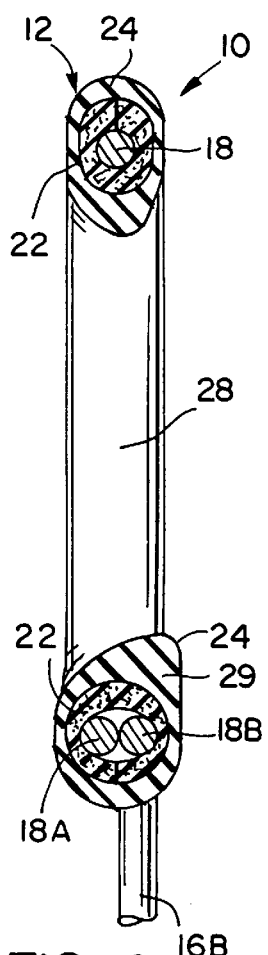
FIG. 4 is a cross-sectional view taken along lines 4—4 in FIG. 2.
Figure 3:
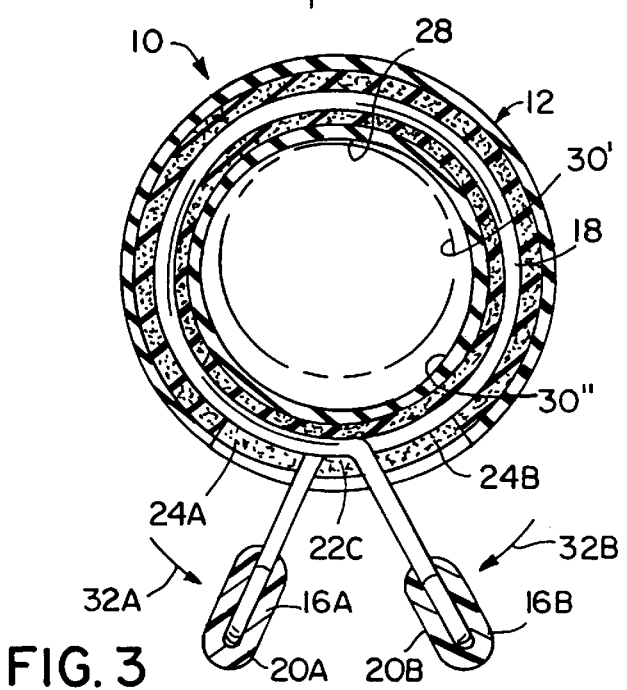
FIG. 3 is a planar sectional view similar to the view shown in FIG. 2 in which handles of the apparatus have been squeezed together to open the apparatus and increase the cross-sectional area of the inner opening through the apparatus.

Referring in particular to FIGS. 2 through 4, the resilient ring member 12 includes a substantially circular spring 18 made of a resilient wire. The resilient wire 18 is preferably a relatively thick stainless steel wire which will retain its original shape even after repeated use. The handles 16A, 16B and the resilient ring member 12 are preferably made from a single continuous piece of wire 18. As mentioned, the ring portion 12 of the wire 18 is preferably substantially circular to conform with the typical geometry of a penis, however, it is not necessary that the ring portion 12 be an exact circle. In fact, prototypes of the invention 10 have been made in which the resilient ring member 12 has a slight racetrack shape. The wire 18 extends from handle 16A circumferentially around the resilient ring member 12 for approximately 450° such that the wire 18 overlaps for an angle α, FIG. 2, which is preferably about 90°. In FIG. 4, the overlap portions of wire 18 are depicted by reference numerals 18A, 18B. Wire portion 18A is contiguous with handle 16A whereas wire portion 18B is contiguous with handle 16B. Each handle 16A, 16B preferably includes a hard epoxy grip 20A, 20B, respectively.

The resilient ring member 12 also preferably includes a cloth mesh substrate 22 wrapped around the substantially circular spring 18. The cloth mesh substrate 22 and the part of the wire 18 commensurate with the resilient ring member 12 are encapsulated in an elastomer, preferably medical grade silicone. The cloth mesh substrate 22 supports the elastomer 24 on the wire 18. The encapsulating elastomer impregnates the supporting substrate 22 and also forms an outer layer of elastomer 24. Note that the cloth mesh supporting substrate is not wrapped around the wire portions 18A, 18B in the regions which would obstruct the range of movements of the handles 16A, 16B. A small portion of cloth mesh substrate is, however, preferably wrapped symmetrically between the handles 16A, 16B to provide structural integrity. The elastomer portions 24A, 24B located within the range of movement of the handles 16A, 16B, respectively, do not contain the cloth mesh supporting substrate 22, but have a slit to facilitate movement of the handles 16A, 16B towards each other. The slits are labeled 26A, 26B in FIGS. 1 and 5.

The layer of elastomer encapsulation 24 defines an inside circumferential surface 28 for the resilient ring member 12. It is preferred that the inside circumferential surface 28 be supple and adapted to contact skin on the shaft of the penis. It is preferred that the inside circumferential surface 28 not be overly slippery. As shown in FIG. 4, it may be desirable for the inside circumferential surface 28 to have a lip 29.

In FIG. 2, the resilient ring member is shown in the closed position in which the inner opening 14 has a minimum cross-sectional area defined by the circumference 30'. In FIG. 3, the handles 16A, 16B are shown squeezed together (arrows 32A, 32B) to open the resilient ring member 12 so that the inside circumferential surface 28 defines a larger cross-sectional area 30". The resilient ring member 12 is biased to remain in the closed position as shown in FIG. 2 such that the cross-sectional area of the inner opening 14 remains at the minimum cross-sectional area 30', unless the handles 16A, 16b are squeezed towards each other.

The minimum cross-sectional area 30' of the inner opening 14 should be selected, preferably by a physician, sufficiently small to restrict return venous blood flow from the penis to the torso when the resilient ring member 18 is in the closed position, see FIG. 2. On the other hand, the size of the inner opening 14 in the closed position, see FIG. 2, should not be so small as to cause significant discomfort.

It should be readily apparent that the apparatus 10 as described thus far can be easily and quickly opened (FIG. 3) and closed (FIG. 2) by the user of the apparatus 10 or his sexual partner. The apparatus 10 is designed to be opened and closed quickly and easily preferably using a thumb and first finger on one of the user's hands.

Figure 5:
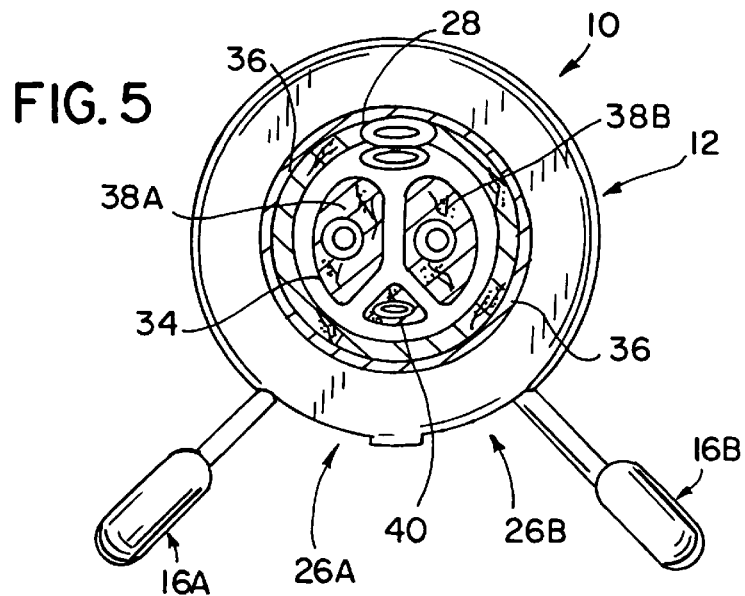
FIG. 5 is an elevational view of the apparatus as it is implemented with the apparatus restricting the return venous flow of blood from the penis to the torso (i.e. restricting excessive venous leakage, the internal anatomy of the penis being shown in cross-section therein.

Referring now in particular to FIG. 5, the apparatus 10 is shown as implemented in the closed position on the penis 34 of the user. As shown in FIG. 5, the supple inside circumferential surface 28 engages the skin 36 of the penis 34, and constricts the penis 34 when in the closed position. The penis 34 is a closed tube comprising three bundles of tissue 38A, 38B, 40 bound together by connective tissue and covered by loose skin 36. The two large bundles of tissue 38A, 38B residing in the upper portion of the penis 34 are the corpora cavemosa. The corpora cavemosa 38A, 38B contains spongy tissue that is filled with blood during sexual excitement thereby causing the penis 34 to become engorged, stiff and erect. Below and between the corpora cavemosa 38A, 38B is a third bundle of tissue 40 which is known as the corpus spongiosum. This bundle contains the urethra. When the apparatus 10 is in the closed position as shown in FIG. 5, the inside circumferential surface 28 of the resilient ring member 12 not only restricts the return venous flow of blood from the penis 34 to the torso, but also restricts flow through the urethra. Therefore, in the embodiment of the invention shown in FIGS. 1–5, the discharge of semen does not occur unless there is a manual release by squeezing the handles 16A, 16B together to enlarge the cross-sectional area of the inner opening 14.

Figure 6A:
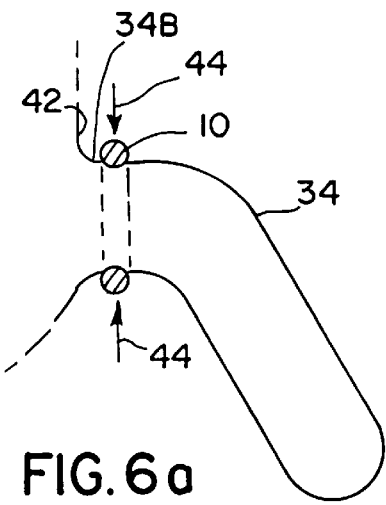
FIGS. 6a–6d illustrate the preferred method of using an apparatus in accordance with the invention to produce and maintain a penile erection in a male suffering from erectile dysfunction.
Figure 6B:
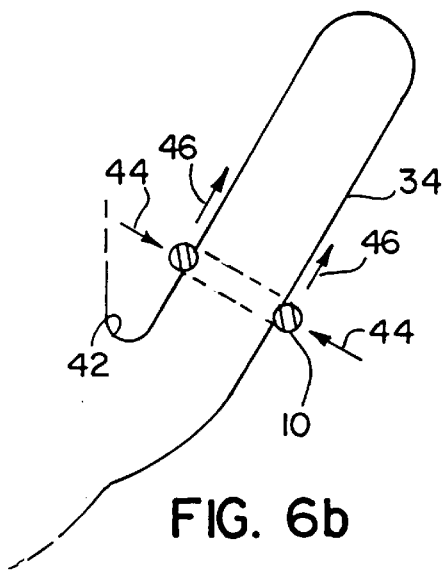
Figure 6C:
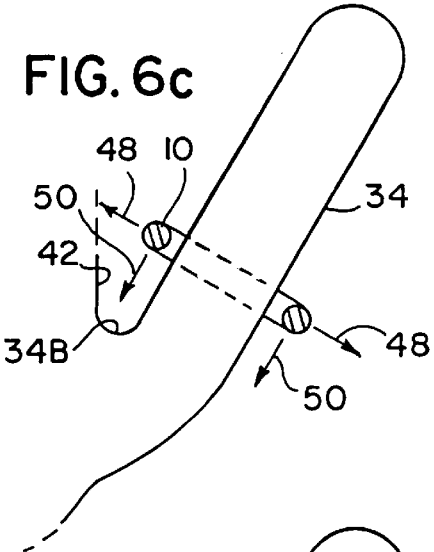
Figure 6D:
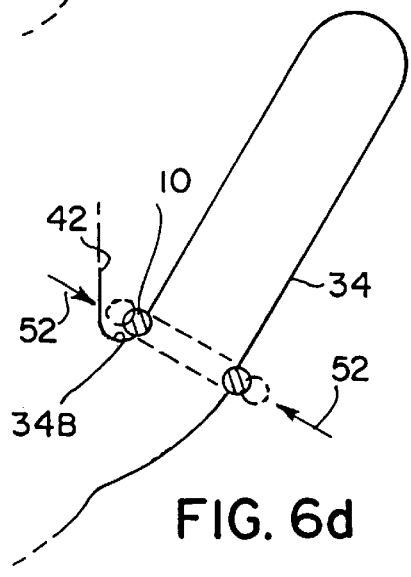

FIGS. 6a–6d show the preferred manner of using the apparatus 10 to produce and maintain a penile erection. First, the apparatus 10 is opened to increase the cross-sectional area of the inner opening 14 of the resilient ring member 18, and the penis 34 is inserted through the inner opening 14 of the resilient ring member 18. The resilient ring member 18 is then placed at the base 34B of the penis 34 adjacent the torso 42 in the closed position, as is depicted by arrows 44 in FIG. 6a. The apparatus 10 is maintained in the closed position, and moved along the penis shaft 34 away from the torso 42 for about 1–2 inches as illustrated in FIG. 6b, arrows 46. This movement increases the amount of engorgement of the portion of the penis 34 on the side of the apparatus 10 opposite the torso 42. Referring now to FIG. 6c, the apparatus 10 is opened, arrows 48, and quickly moved towards the base of the penis 34B adjacent the torso 42, arrows 50. When the apparatus 10 is moved to the base 34B of the penis 34 adjacent the torso 42, the apparatus 10 is closed, arrows 52 in FIG. 6d. The steps shown in FIG. 6b through FIG. 6d are repeated as necessary to incrementally capture enough blood within the penis 34 on the side of the apparatus 10 opposite the torso 42 to produce a suitable erection of the penis 34. If the apparatus 10 is sized properly, a user of the apparatus and their partner can achieve full erection suitable for sexual penetration and enjoyment within 2 to 10 minutes depending on the amount of sexual arousal. After sufficient blood has been captured in the penis 34, the apparatus 10 is placed in the closed position at the base 34B of the penis adjacent the torso 42 to maintain the erection.

The apparatus 10 is especially designed to facilitate efficient erections. In particular, the apparatus 10 is designed so that the user can use one hand to open and close the resilient ring member 18 via handles 16A, 16B. This allows the user's other hand to be available for holding the penis 34 while moving the apparatus 10 towards the torso 42. When the apparatus 10 is in the closed position, the handles 16A, 16B are biased in the closed position and the user is able to use both hands to move the apparatus 10 away from the base 34B of the penis 34. It should be noted that the skin 36 on the penis 34 is loose, and therefore it is not necessary for the apparatus 10 to actually slip or slide with respect to the skin on the shaft of the penis when implementing the above-described method. In fact, it is preferred that the inside circumferential surface 28 of the resilient ring member 18 generally remain in contact with the skin 36 of the penis 34 when using the apparatus to attain erection. In any event, it is desirable that the inside circumferential surface 28 of the apparatus 10 be made of a material, such as medical grade silicone, which does not irritate the base 34B of the penis 34.

It is recognized that modified versions of the apparatus 10 may be suitable for implementing the method shown in FIGS. 6a–6d. That is, the structural components of the apparatus 10 may be modified or changed without departing from the true spirit of the invention. Such modifications, variations or alternatives should be considered to come within the scope of the following claims.

I claim:

1. A method of producing and maintaining a penile erection in a male suffering from erectile dysfunction, the method comprising the steps of:

a) providing a resilient ring member having an inner opening therethrough, the cross-sectional area of the inner opening being adjustable between a minimum cross-sectional area when the resilient ring member is in a fully closed position and larger cross-sectional areas when the resilient ring member is in a partially or fully open position, the minimum cross-sectional area of the inner opening of the resilient ring member being sized sufficiently small to restrict blood flowing from the penis when the resilient ring member is in the closed position;

b) opening the resilient ring member to increase the cross-sectional area of the inner opening through the resilient ring member, inserting the penis through the inner opening of the resilient ring member, and placing the resilient ring member at the base of the penis adjacent the torso;

c) closing the resilient ring member so that the resilient ring member restricts blood flowing from the penis when the resilient ring member is placed at the base of the penis adjacent the torso;

d) moving the resilient ring member along the penis shaft away from the torso while maintaining the resilient ring member in the closed position, thereby increasing the amount of engorgement of the portion of the penis on the side of the resilient ring member opposite the torso;

e) opening the resilient ring member and quickly moving the resilient ring member to the base of the penis adjacent the torso;

f) repeating steps c), d) and e) as necessary to incrementally capture enough blood within the penis on the side of the resilient ring member opposite the torso to produce a suitable erection of the penis;

g) after enough blood has been captured in the penis to produce a suitable erection of the penis, placing the resilient ring member at the base of the penis adjacent the torso in a closed position to maintain the erection.

2. A method of producing and maintaining a penile erection in a male suffering from erectile dysfunction as recited in claim 1 wherein step e) is implemented by the user of the resilient ring member in the following manner:

the user uses one hand to open the resilient ring member and move the resilient ring member to the base of the penis adjacent the torso and the user uses another hand to hold the penis while moving the resilient ring member towards the torso.

3. A method of producing and maintaining a penile erection in a male suffering from erectile dysfunction as recited in claim 1 wherein step d) is implemented by the user of the resilient ring member in the following manner:

the user uses both hands to move the resilient ring member away from the base of the penis adjacent the front torso for approximately 1 to 2 inches along the shaft of the penis.

* * * * *